(12) United States Patent
Tezuka et al.

(10) Patent No.: US 7,377,150 B2
(45) Date of Patent: May 27, 2008

(54) ANALYZER

(75) Inventors: Fuminobu Tezuka, Yokohama (JP);
Yoshiyuki Isozaki, Tokyo (JP); Yasuko Noritomi, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 213 days.

(21) Appl. No.: 11/230,487

(22) Filed: Sep. 21, 2005

(65) Prior Publication Data
US 2006/0216205 A1  Sep. 28, 2006

(30) Foreign Application Priority Data
Mar. 24, 2005   (JP)   ............... 2005-085978

(51) Int. Cl.
*G01N 30/68*   (2006.01)
*G01N 27/416*   (2006.01)
(52) U.S. Cl. ............... 73/23.4; 73/23.41; 73/23.42; 422/54; 422/80; 422/89
(58) Field of Classification Search ............... 73/23.4, 73/23.41, 23.42; 422/54, 80, 89
See application file for complete search history.

(56) References Cited

U.S. PATENT DOCUMENTS

| | | | | |
|---|---|---|---|---|
| 4,534,207 A | * | 8/1985 | Szakasits et al. | ......... 73/23.38 |
| 5,082,473 A | * | 1/1992 | Keefer | ............ 95/98 |
| 6,422,056 B1 | * | 7/2002 | Miyai et al. | ......... 73/1.06 |
| 2004/0062961 A1 | | 4/2004 | Sato et al. | ......... 429/19 |
| 2004/0247960 A1 | | 12/2004 | Sato et al. | ......... 429/20 |
| 2005/0008907 A1 | | 1/2005 | Isozaki et al. | ......... 429/20 |
| 2005/0214163 A1 | | 9/2005 | Kinpara et al. | |

FOREIGN PATENT DOCUMENTS

| | | |
|---|---|---|
| JP | 8-211038 | 8/1996 |
| JP | 2003-88754 | 3/2003 |
| JP | 2004-127624 | 4/2004 |
| JP | 2004-127625 | 4/2004 |
| JP | 2004-127626 | 4/2004 |
| JP | 2004-303695 | 10/2004 |
| JP | 2004-319467 | 11/2004 |
| JP | 2004-342413 | 12/2004 |

\* cited by examiner

*Primary Examiner*—Daniel S Larkin
(74) *Attorney, Agent, or Firm*—Oblon, Spivak, McClelland, Maier & Neustadt, P.C.

(57) ABSTRACT

An analyzer includes a reforming unit which reforms fuel containing an organic compound which contains carbon and hydrogen into a reformed gas containing hydrogen, a flame ionization detector which is connected to the reforming unit, and detects an ion generated by combusting the reformed gas supplied from the reforming unit and a sample gas, or ionizing a sample gas by reaction with the reformed gas supplied from the reforming unit, and outputs an output signal representing the ionic amount, and an analysis controller which analyzes the output signal from the flame ionization detector, and provides data capable of identifying a component contained in the sample gas.

8 Claims, 6 Drawing Sheets

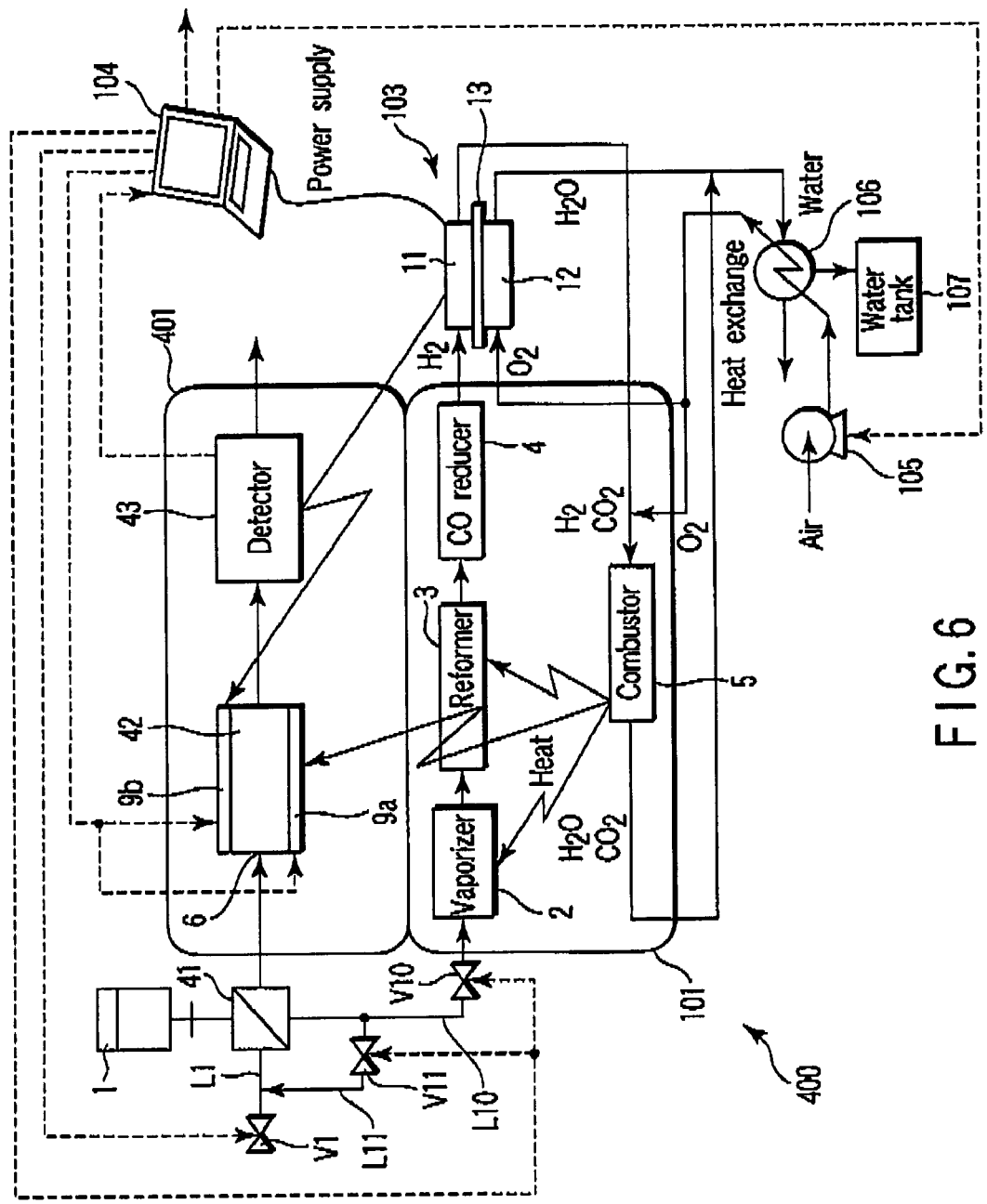
F I G. 6

ANALYZER

CROSS-REFERENCE TO RELATED APPLICATIONS

This application is based upon and claims the benefit of priority from prior Japanese Patent Application No. 2005-085978, filed Mar. 24, 2005, the entire contents of which are incorporated herein by reference.

BACKGROUND OF THE INVENTION

1. Field of the Invention

The present invention relates to an analyzer.

2. Description of the Related Art

Recently, environmental protection activities are becoming much more pronounced. This increases the number of opportunities to perform various analyses on samples existing outdoors, such as the atmosphere, water in rivers and the like, and soil. Especially when changes in sample with time are to be analyzed outdoors, when a sample is to be analyzed immediately after being sampled, or when subsequent sampling is to be performed in accordance with the obtained measurement, a safe, portable analytical system which is compact and lightweight and can be carried to a sampling point is necessary.

As an analyzer for analyzing these samples existing outdoors, e.g., for the analysis of gases, a gas chromatograph analytical system is used. In the conventional gas chromatograph analytical system, heating is performed to separate the component of a sample gas. For example, Jpn. Pat. Appln. KOKAI Publication No. 8-211038 describes that a portable analyzer is implemented by obtaining heat necessary for this heating by using the exothermic reaction of a combustion gas.

In the gas chromatograph analytical system, a flame ionization detector (FID) can be used as an analyzer for analyzing a sample gas. Hydrogen gas is necessary to analyze a sample gas by using this FID. Since, however, hydrogen gas is explosive, the transportation, storage, or use of hydrogen gas requires a rigid and safe vessel and vehicle, and further requires a vessel, worker, and storage facility which comply with the law. Therefore, the conventional analyzer cannot simply transport nor handle hydrogen gas.

There are some gas chromatograph analyzers in which hydrogen is generated in its actual use, and then the generated hydrogen is used in analysis. More specifically, hydrogen is generated by a hydrogen generator which generates hydrogen by electrolyzing water.

Unfortunately, the hydrogen generator is mainly used in a stationary analyzer because the generation of hydrogen requires high power. To transport the hydrogen generator and use it in analysis, a power supply for obtaining high power must be transported at the same time. This makes the hydrogen generator difficult to transport.

It is an object of the present invention to provide an analyzer which is compact, lightweight, and easy to handle.

BRIEF SUMMARY OF THE INVENTION

According to one aspect of the present invention, there is provided an analyzer comprising a reforming unit which reforms fuel containing an organic compound which contains carbon and hydrogen into a reformed gas containing hydrogen, a fuel cell which is connected to the reforming unit, and generates power by using the reformed gas supplied from the reforming unit and oxygen, a flame ionization detector which is connected to the reforming unit, and detects an ion generated by combusting the reformed gas supplied from the reforming unit and a sample gas, and an analysis controller which is connected to the fuel cell, operates by using the power generated by the fuel cell, analyzes an output signal from the flame ionization detector, and provides data capable of identifying a component contained in the sample gas.

According to another aspect of the present invention, there is provided an analyzer comprising a reforming unit which reforms fuel containing an organic compound which contains carbon and hydrogen into a reformed gas containing hydrogen, a fuel cell which is connected to the reforming unit, and generates power by using the reformed gas supplied from the reforming unit and oxygen, a reducing unit which is connected to the reforming unit, and reduces a component contained in a sample fluid by using the reformed gas supplied from the reforming unit, a detector which is connected to the reducing unit, and detects the component reduced in the reducing unit, and an analysis controller which is connected to the fuel cell, operates by using the power generated by the fuel cell, analyzes an output signal from the detector, and provides data capable of identifying the component contained in the sample fluid.

According to another aspect of the present invention, there is provided an analyzer comprising a reforming unit which reforms fuel containing an organic compound which contains carbon and hydrogen into a reformed gas containing hydrogen, a fuel cell which is connected to the reforming unit, and generates power by using the reformed gas supplied from the reforming unit and oxygen, a reference electrode connected to the reforming unit, and dipped in a sample liquid into which the reformed gas is supplied from the reforming unit, a counter electrode and working electrode dipped in the sample liquid, an electrochemical instrumentation which is connected to the reference electrode, working electrode, and counter electrode, and performs electrochemical measurement, and an analysis controller which is connected to the fuel cell, operates by using the power generated by the fuel cell, analyzes an electrochemical measurement signal output from the electrochemical instrumentation, and provides data capable of identifying a component contained in the sample liquid.

According to another aspect of the present invention, there is provided an analyzer comprising a reforming unit which reforms fuel containing an organic compound which contains carbon and hydrogen into a reformed gas containing hydrogen, a working electrode and counter electrode dipped in a sample liquid, a normal hydrogen electrode which is indirectly connected to the sample liquid via a salt bridge electrically, and connected to the reforming unit from which the reformed gas can be supplied, an electrochemical instrumentation which is connected to the normal hydrogen electrode, working electrode, and counter electrode respectively, and performs electrochemical measurement, and an analysis controller which analyzes an electrochemical measurement signal output from the electrochemical instrumentation, and provides data configured to identify a component contained in the sample liquid.

Furthermore, according to another aspect of the present invention, there is provided an analyzer comprising a reforming unit which reforms fuel containing dimethylether in a liquid state into a reformed gas containing hydrogen, a fuel cell which is connected to the reforming unit, and generates power by using the reformed gas supplied from the reforming unit and oxygen, a separator which separates a component contained in a sample liquid, pressurizing means for applying, to the sample liquid, a pressure generated by the dimethylether, thereby supplying the sample liquid to the separator, a detector which is connected to the separator, and detects the component separated in the separator, and an analysis controller which operates by using the power generated by the fuel cell, analyzes an output signal from the detector, and provides data capable of identifying the component contained in the sample liquid.

BRIEF DESCRIPTION OF THE SEVERAL VIEWS OF THE DRAWING

FIG. 6 is a block diagram schematically showing an analyzer according to a fourth embodiment of the present invention.

DETAILED DESCRIPTION OF THE INVENTION

Figure 1:
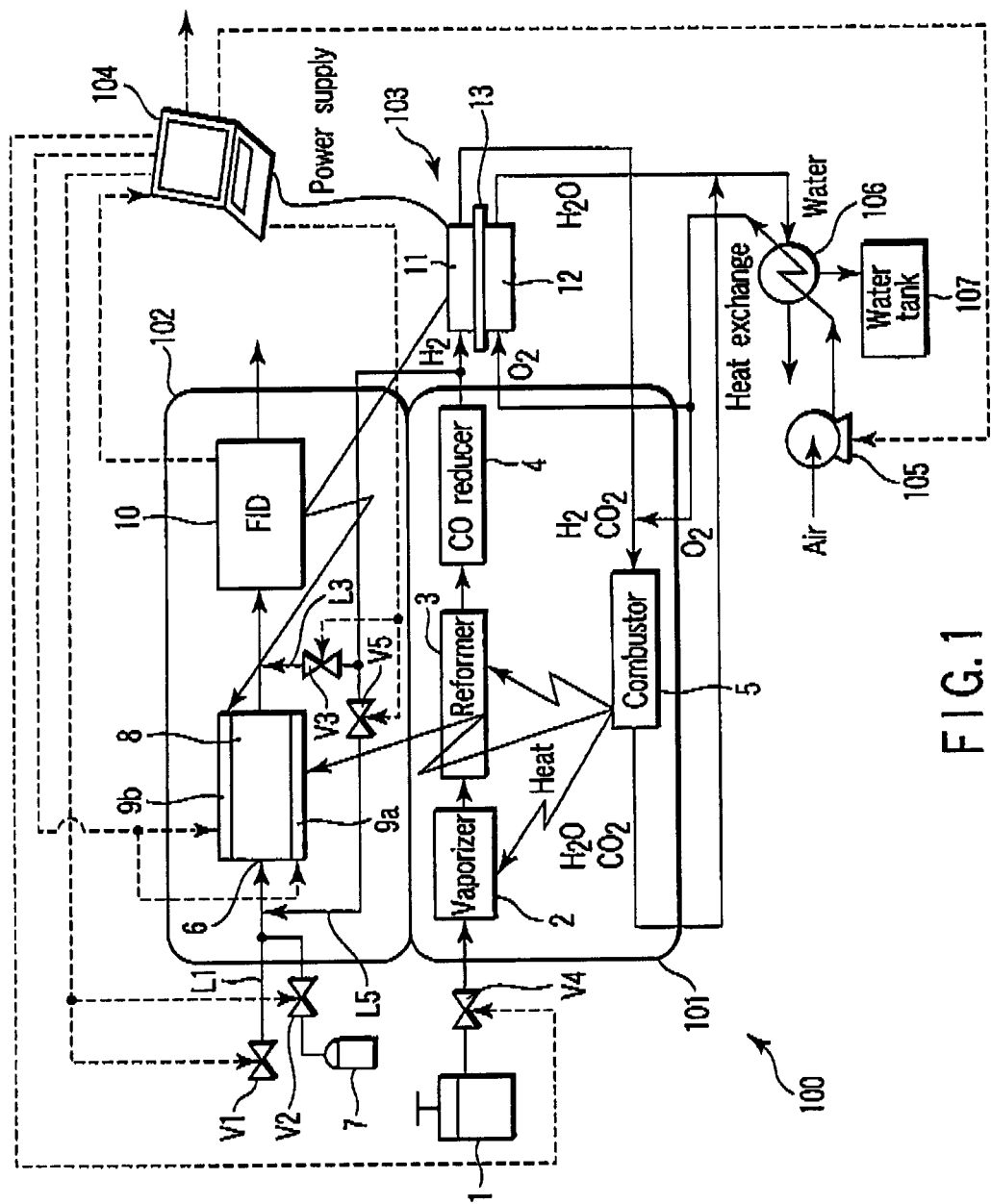
FIG. 1 is a block diagram schematically showing an analyzer according to a first embodiment of the present invention.

Embodiments of the present invention will be described in detail below with reference to the accompanying drawings. Note that in the drawings, the same reference numerals denote constituent elements which achieve the same or similar functions, and a repetitive explanation thereof will be omitted.

First Embodiment

FIG. 1 is a block diagram schematically showing an analyzer according to a first embodiment of the present invention.

An analyzer 100 of the first embodiment includes a reforming unit 101, analyzing unit 102, fuel cell 103, and analysis controller 104. Hydrogen generated in the reforming unit 101 is used in the analyzing unit 102 in order to analyze a sample gas. This generated hydrogen is also used in the fuel cell 103 which generates electric power by using the hydrogen. The generated power is used in the analysis controller 104 for the purpose of analysis. More specifically, this generated power is used as at least a part of electric power necessary for the analysis controller 104 to, e.g., amplify or analyze an output signal from the analyzing unit 102. This power is also used as at least a part of electric power necessary to operate, e.g., the reforming unit 101, analyzing unit 102, or fuel cell 103.

The analyzer 100 further includes a pump 105, heat exchanger 106, and water tank 107. The pump 105 supplies air containing oxygen to the fuel cell 103. The heat exchanger 106 exchanges heat between the air used in power generation in the fuel cell 103 and the air to be supplied to the fuel cell 103. The water tank 107 collects water condensed in the heat exchanger 106. The electric power generated by the fuel cell 103 can be used as to operate the pump 105.

Details of the reforming unit 101 will be explained below.

The reforming unit 101 has a vaporizer 2 for vaporizing at least a portion of liquid fuel supplied from a fuel tank 1. The fuel tank 1 contains organic fuel (to be simply referred to as fuel hereinafter), e.g., an aqueous solution of an organic compound containing carbon and hydrogen. Examples of the organic compound are alcohol, such as methanol and ethanol, naphtha, and dimethylether. The vaporizer 2 can vaporize the fuel by using heat supplied by a combustor 5 (to be described later).

The reforming unit 101 has a reformer 3. The reformer 3 is connected to the downstream side of the vaporizer 2. The reformer 3 promotes a reforming reaction which reforms the fuel vaporized by the vaporizer 2 into a gas (a reformed gas) containing hydrogen. The reformer 3 is filled with a reforming catalyst which promotes the reforming reaction of the vaporized fuel. The reforming reaction can be further accelerated by supplying heat from the combustor 5 (to be described later) to the reformer 3. It is also possible to heat the reformer 3 by using heat of, e.g., the fuel cell 103, an electric heater (not shown), or the combustion of the fuel, instead of or in combination with the heat of the combustor 5. When an aqueous solution of dimethylether and water is used as the fuel, it is possible to use, as the reforming catalyst, Pt, Cu, Zn, a mixture of Pd/ZnO or Cu/ZnO, and alumina, or a reforming catalyst having Pt/alumina. When an aqueous solution of dimethylether and water is used as the fuel, the reforming reaction is $$CH_3OCH_3 + 3H_2O \rightarrow 6H_2 + 2CO_2(+CO) \quad (1)$$

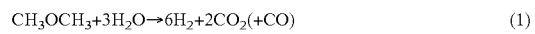

wherein CO is carbon monoxide as a byproduct.

The reforming unit 101 further has a CO reducer 4. The CO reducer 4 is connected to the downstream side of the reformer 3. The fuel obtained after the reforming reaction is promoted in the reformer 3, i.e., the reformed gas, sometimes contains a large amount of CO as a byproduct. The CO reducer 4 reduces the concentration of CO contained in the reformed gas. The CO reducer 4 is filled with a CO reducing catalyst which promotes the reaction which shifts from CO to another material, e.g., a CO water gas shift reaction or a selective methanation reaction. As a CO reducing reaction, a reaction indicated by formula (2) or (3) can be used. A CO reducing catalyst containing Pt can be used for the reaction of formula (2), and a CO reducing catalyst containing Mg or Ru can be used for the reaction of formula (3).

$$CO + H_2O \rightarrow H_2 + CO_2 \quad (2)$$

$$CO + 3H_2 \rightarrow CH_4 + H_2O \quad (3)$$

The reformed gas in which the CO concentration is thus reduced is supplied to the analyzing unit 102 and fuel cell 103 connected to the reforming unit 101. The heat generated during the CO reducing reaction in the CO reducer 4 can also be supplied to the vaporizer 2.

A portion of hydrogen contained in the reformed gas supplied to the fuel cell 103 is used in power generation. The reformed gas exhausted from the fuel cell 103 contains the rest of hydrogen not used in the power generation. This reformed gas exhausted from the fuel cell 103 is supplied to the combustor 5.

The combustor 5 accelerates an oxidation reaction of the rest of hydrogen contained in the reformed gas exhausted from the fuel cell 103. The combustor 5 is contained with a combusting catalyst. This combusting catalyst accelerates the oxidation reaction of the remaining hydrogen, so it changes into water (steam). Oxygen necessary for the oxidation reaction is supplied in the form of oxygen containing air to the combustor 5 by the pump 105. The combustor 5 reaches a temperature of, e.g., about 350° C. As described above, the heat generated during the oxidation reaction can be supplied to the vaporizer 2, reformer 3, or CO reducer 4. Heat conducting members 9a and 9b can be provided between the combustor 5, and the vaporizer 2, reformer 3, or CO reducer 4. The heat generated during the oxidation reaction can also be supplied to a column 8 (to be described later) by using a heat conducting member 9a (to be described later). The gas (steam) exhausted from the combustor 5 has a temperature of, e.g., about 300° C. Therefore, the heat of the gas (steam) exhausted from the combustor 5 may also be supplied to at least one of the vaporizer 2, reformer 3, CO reducer 4, and column 8, instead of or in combination with the heat of the combustor 5. Although FIG. 1 shows an example in which the combustor 5 is incorporated into the reforming unit 101, this embodiment is not limited to this example. That is, the combustor 5 can be contained in the reforming unit 101, or externally attached to the reforming unit 101 or fuel cell 103.

Note that the reforming unit 101 including the combustor 5 can be stowed in a heat-insulated vessel. When a catalyst of a copper-zinc family is used as the reforming catalyst, the temperature of the reformer 3 is preferably set at, e.g., about 250° C. When a Pt catalyst, for example, is used as the reforming catalyst, the reformer 3 is preferably set at, e.g., about 350° C. The heat of the combustor 5 can be efficiently conducted to the reformer 3 or vaporizer 2 by carrying the reforming unit 101 in a heat-insulated vessel.

Details of the analyzing unit 102 will be explained below.

The analyzing unit 102 has a supply port 6 for supplying a sample gas. A carrier gas supply 7 can be connected to a line L1 on the upstream side of the supply port 6. The carrier gas supply 7 helps supply a sample gas into the analyzing unit 102. As the carrier gas supply 7, it is possible to use, e.g., a structure obtained by connecting a regulator to a cylinder filled with an inert gas, such as He or $N_2$.

The analyzing unit 102 can have the column 8 as a separating means for separating a sample gas. When the composition of gas contained in a sample gas is already known, the column 8 is not particularly necessary. However, if the type of gas contained in a sample gas is unknown, or if the type of gas changes, the column 8 is preferably placed in the analyzing unit 102. As this separating means, a gas chromatography column can be used. In particular, a capillary column or packed column can be used as the column 8. This capillary column or packed column can have, e.g., a molecular sieve function.

A first heat conducting member 9a is provided as a heat transfer means between the column 8 and combustor 5. The column 8 and combustor 5 can be thermally connected via the first heat conducting member 9a. As the heat conducting member 9a, it is possible to use, e.g., a metallic plate made of metal having a high conductivity, e.g., aluminum or copper, heat pipe, or heat exchanger using a heating medium, such as a fluid. However, the heat conducting member 9a of this embodiment is not limited to these materials, and it is also possible to use materials, such as plastic having a relatively low heat conductivity. The heat conducting member 9a may also be integrated with the combustor 5 or reforming unit 101, or with a protection case of the column 8. The column 8 is heated by heat supplied from the combustor 5 to the column 8 by the heat conducting member 9a. This allows the column 8 to separate components contained in the sample gas. The column 8 may be thermally connected to the combustor 5 via the heat conducting member 9a by using a heating medium fluid, such as a liquid or gas, alternative to a solid member.

The analyzing unit 102 has a flame ionization detector (FID) 10. The FID 10 is connected to the column 8 so that the sample gas separated into components can be supplied to the FID 10. The FID 10 is also connected to the reforming unit 101 so that the reformed gas can be supplied to the FID 10. The FID 10 combusts the sample gas separated into components, and the reformed gas, or ionizes the sample gas separated into components by reaction with the reformed gas. The FID 10 also detects ions generated during the combustion or ionization, and outputs an output signal representing ionic amount.

Details of the fuel cell 103 will be explained below.

The fuel cell 103 includes an MEA having a structure in which an electrolyte membrane 13 is sandwiched between a fuel electrode 11 and oxidizer electrode 12. It is possible to use only one MEA, or combine a plurality of MEAs. The fuel electrode (or anode) 11 contains, for example, a porous sheet which holds a carbon black powder supporting Pt by a water repellent resin binder, such as polytetrafluoroethylene (PTFE). Similar to the fuel electrode 11, the oxidizer electrode (or cathode) 12 contains, for example, a porous sheet which holds a carbon black powder supporting Pt by a water repellent resin binder such as polytetrafluoroethylene (PTFE). The electrolyte membrane 13 is made of a fluorocarbon polymer, e.g., NAFION (a registered trademark of Du Pont), having a cation exchange group such as a sulfonic acid group or carboxylic acid group, and has proton conductivity. The porous sheet of the fuel electrode 11 and oxidizer electrode 12 may contain a sulfonic acid type perfluorocarbon polymer or fine particles coated with this polymer.

The reformed gas is supplied to the fuel electrode 11 from the reforming unit 101. This reformed gas is used in power generation in the fuel electrode 11, and supplied to the combustor 5. Also, air (having undergone heat exchange in the heat exchanger 106) is supplied to the oxidizer electrode 12 by using the pump 105. This air is used in power generation in the oxidizer electrode 12, and supplied to the heat exchanger 106.

Hydrogen in the reformed gas supplied to the fuel electrode 11 reacts in it as indicated by

$$H_2 \rightarrow 2H^+ + 2e^- \qquad (4)$$

On the other hand, oxygen in the air supplied to the oxidizer electrode 12 reacts in it as indicated by

$$\tfrac{1}{2}O_2 + 2H^+ + 2e^- \rightarrow H_2O \qquad (5)$$

A second heat conducting member 9b is provided as a heat transfer means between the fuel cell 103 and column 8. The fuel cell 103 and column 8 can be thermally connected via the second heat conducting member 9b. As the heat conducting member 9b, it is possible to use, e.g., a metallic plate made of metal having a high conductivity, e.g., aluminum or copper, heat pipe, or heat exchanger using a heating medium, such as a fluid. However, the heat conducting member 9b of this embodiment is not limited to these materials, and it is also possible to use materials, such as plastic having a relatively low heat conductivity. The heat conducting member 9b may also be integrated with the fuel cell 103, or with a protection case of the column 8.

Details of the analysis controller 104 will be explained below.

As the analysis controller 104, a general purpose information processing terminal, such as a personal computer and its peripheral devices, can be used. An output signal from the FID 10 is an analog signal having a small current value. The analysis controller 104 converts this output signal into a digital signal, and, if necessary, amplifies the output signal before converting it into a digital signal. Also, the analysis controller 104 performs necessary processing on the output signal thus converted into a digital signal, in accordance with, e.g., the analysis purpose or the type of sample gas, and outputs the result of analysis. For example, a component (an analytic component) contained in a sample gas can be identified (qualitatively and/or quantitatively determined) from the result of analysis. This identification can be performed by referring to a prepared database of the analysis controller 104. Alternatively, whenever a sample gas is analyzed, the analytic component described above can be calibrated by analyzing a standard sample (not shown) by the analyzing unit 102.

The obtained signal can be physically stored in a recording medium, such as a hard disk, of the analysis controller 104. Depending on the state of changes in sample fluid, an exhaust source which exhausts the sample fluid can be controlled to stop the exhaustion. The state of a sample fluid can also be globally monitored by communicating with another observation base via a network by using wires or by radio.

The analysis controller 104 can also perform necessary control for operating the analyzer 100, e.g., the reforming unit 101 and analyzing unit 102, the control is such as carrier gas flow rate control and sequence control of the operation of the analyzing unit 102. Practical analysis control is as follows.

First, the analysis controller 104 determines whether the analyzing unit 102 is capable of analysis. Examples of the determination items are the remaining amount of a carrier gas, the temperature and pressure of a sample gas, the temperature of the column 8, the temperature of the FID 10, and the stability of the baseline of an ionic electric current of the FID 10. The analysis controller 104 totally evaluates these determination items, and, if a problem arises, performs feedback control such that each item falls within a predetermined range. The determination standards can be pre-stored in the analysis controller 104 or externally supplied by communication.

If the analysis state of the analyzing unit 102 has no problem, a sample gas is supplied into the analyzing unit 102 from the supply port 6. The analysis controller 104 can also control, e.g., the supply amount of the sample gas. For example, the analysis controller 104 can control the ratio of the sample gas to the carrier gas by controlling a valve V1 of the line L1 on the upstream side of the supply port 6 and a valve V2 on the downstream side of the carrier gas supply means 7. In this manner, an appropriate amount of sample gas can be supplied to the analyzing unit 102.

The appropriate amount of sample gas is supplied to the separating means through the supply port 6, i.e., the supply port of the reforming unit 101. Although the column 8 is used as this separating means in this embodiment, the present invention is not limited to this embodiment. The column 8 can be used as it is held at a predetermined temperature, or can be used as it is heated at a predetermined heating rate and then held at a predetermined temperature. The method of using the column 8 can be changed in accordance with the type of sample gas.

The reforming unit 101 can be used as a heating source of the column 8. The quantity of heat supplied to the column 8 can be controlled by the analysis controller 104. For example, when the molecular weights of target component contained in a sample gas extend over a broad range, it is preferable to heat the column 8 at a constant rate of 5° C./min in order to perform analysis with a short time. It may also be necessary to heat the column 8 to a predetermined temperature of, e.g., 300° C. When the molecular weights of target component contained in a sample gas extend over a broad range, the temperature of the column 8 can be increased by supplying heat to the column 8 from the reforming unit 101, particularly, the combustor 5.

On the other hand, when a sample gas is made up of only components, such as methane or ethane, having relatively low molecular weights, these components can be separated in a constant temperature use environment at 80° C. or less. In this case, the column 8 can be controlled at a constant temperature by supplying the heat of the fuel cell 103 to the column 8, while the heat is controlled by the analysis controller 104. Because the fuel cell 103 generates heat at a temperature of 60° C. to 90° C. The quantity of heat generated by the fuel cell 103 can be adjusted, for example, by controlling the fuel supply amount from the fuel tank 1 via a valve V4 (to be described later) or by controlling the oxygen supply amount by the pump 105. The heat supplied from the fuel cell 103 to the column 8 can be the heat of the fuel electrode 11 or the heat of the oxidizer electrode 12. This heat can also be the heat of the whole of the fuel cell 103. It is, of course, also possible to supply a deficient heat quantity from the reforming unit 101 or a heater (not shown).

When heat is to be supplied from the combustor 5 to the column 8, at least one of the first heat conducting member 9a, combustor 5, and column 8 is moved by a cylinder driving mechanism (not shown) to bring the first heat conducting member 9a into contact with both the combustor 5 and column 8. In this way, heat can be supplied from the combustor 5 to the column 8. When the heating medium is used as the first heat conducting member 9a, a heating medium valve (not shown) is opened to supply the fluid from the combustor 5 serving as a high-temperature portion to the column 8 serving as a low-temperature portion. This makes it possible to transfer heat from the combustor 5 to the column 8.

On the other hand, when heat is to be supplied from the fuel cell 103 to the column 8, at least one of the second heat conducting member 9b, fuel cell 103, and column 8 is moved by a cylinder driving mechanism (not shown) to bring the second heat conducting member 9b into contact with both the fuel cell 103 and column 8. In this manner, heat can be supplied from the fuel cell 103 to the column 8. The heating medium can also be used as the second heat conducting member 9b in the same manner as described above. That is, a heating medium valve (not shown) is opened to supply the fluid from the fuel cell 103 serving as a high-temperature portion to the column 8 serving as a low-temperature portion. This makes it possible to transfer heat from the fuel cell 103 to the column 8. Note that in this embodiment, the first and second heat conducting members 9a and 9b are placed in the column 8. However, the heat conducting members 9a and 9b may also be placed in the reforming unit 101 and fuel cell 103, respectively. It is also possible to omit one of the heat conducting members 9a and 9b.

The analysis controller 104 can switch a heat conduction mode using the first heat conducting member 9a and a heat conduction mode using the second heat conducting member 9b, in accordance with a sample gas. That is, when a sample gas is to be analyzed as it is heated to a high temperature, the analysis controller 104 selects the heat conduction mode using the first heat conducting member 9*a*. When a sample gas is to be analyzed as it is heated to a low temperature, the analysis controller 104 selects the heat conduction mode using the second heat conducting member 9*b*. Note that in FIG. 1, the conduction of heat is indicated by the zigzag solid lines. Also, the exchange of fluid is indicated by the solid lines, and the transmission of signals is indicated by the dotted lines.

A necessary heat quantity of the column 8 can be controlled by dividing the combustor 5 into a plurality of portions different in heat capacity. That is, when the combustor 5 is divided into three portions A, B, and C, the heat capacities of the portions A, B, and C are set at, e.g., 2, 1, and 0.5 W, respectively. When a heat capacity of about 3 W is necessary, the portions A and B are operated. When a heat capacity of about 1.5 W is necessary, the portions B and C are operated. This makes it possible to control both the heat capacity of the combustor 5 and the temperature of the column 8. If the temperature of the column 8 rises more than necessary, at least one of the portions A, B, and C need only be turned off. The analysis controller 104 can perform all these control operations.

Note that when the column 8 is to be cooled after the analysis, the analysis controller 104 can direct and supervise the control. The column 8 can be cooled by supplying air to the periphery of the vessel of the column 8 (when an oven [not shown] for heating the column 8 is used, air is supplied into this oven). It is also possible to provide a cooler (not shown), and cool the column 8 by this cooler. Alternatively, another heat conducting member (e.g., a heat radiation fin [not shown]) can be attached to the column 8 to obtain a structure which misses heat to the outside.

A sample gas separated into components by the separating means, such as the column 8, is successively supplied to the FID 10. The gas is mixed with a predetermined amount of the reformed gas supplied from the reforming unit 101, and an output signal is obtained as a flame ionization current. On the basis of this output signal, the concentration of each component in the sample gas can be quantitatively and continuously detected. Note that the flow rate of the reformed gas supplied from the reforming unit 101 to the analyzing unit 102 can also be controlled by the analysis controller 104. More specifically, when the analysis controller 104 controls a valve V3 provided in a reformed gas supply channel, the flow rate of the reformed gas from the reforming unit 101 to the analyzing unit 102 is controlled.

It is possible to use one or a plurality of analysis controllers 104. When one analysis controller 104 is used, the analysis controller 104 performs analysis and control of the whole of the analyzer 100. When a plurality of analysis controllers 104 are used, the analysis controllers 104 analyze and control the reforming unit 101, analyzing unit 102, and fuel cell 103 by complementing each other. The analysis control method of the analysis controller 104 can be preset as a program in the analysis controller 104. On the basis of the set program, the operation of each unit of the analyzer 100 can be controlled.

If the analyzing unit 102 becomes incapable of analysis, the analysis controller 104 can analyze information of this inconvenience. On the basis of this analytical result, the analysis controller 104 can perform control so as not to supply the reformed gas containing hydrogen from the reforming unit 101 to the analyzing unit 102. The analysis controller 104 can also generate an alarm indicating the inconvenient state, and notify another station of the inconvenient state via a network by using a telephone line or by radio.

Note that electric power necessary to operate the analysis controller 104 can be supplied from the fuel cell 103. Note also that electric power necessary to operate the reforming unit 101 and/or the analyzing unit 102 can be supplied from the fuel cell 103. It is also possible to combine the fuel cell 103 and an external power supply to obtain a combined power supply system which supplies electric power necessary to operate the analyzer 100. Furthermore, the fuel cell 103 alone can be used as a private power generation system which supplies all electric power necessary to operate the analyzer 100.

The reforming unit 101 generates hydrogen necessary for the analyzing unit 102 and hydrogen necessary for the fuel cell 103. The analysis controller 104 monitors, measures, and analyzes the analysis intervals of the analyzing unit 102, and the power consumption and demand quantity of heat including peripheral devices and the like. On the basis of the result of analysis, the analysis controller 104 can control the amount of fuel to be supplied, and the amount of hydrogen to be generated. The analysis controller 104 controls the amount of fuel supplied to the reforming unit 101. More specifically, the supply amount of fuel is controlled when the analysis controller 104 controls the valve V4 on the exit side of the fuel supply tank 1.

When the analyzer 100 of the first embodiment is to be transported in order to analyze a sample fluid existing outdoors, it is unnecessary to transport hydrogen or a power supply required when a hydrogen generator electrolyzes water. This makes the analyzer 100 compact, lightweight, and easy to handle.

In addition, since heat for heating the separating means is supplied from the combustor 5, it is possible to reduce the heating capability of the electric heater for heating the separating means, or it is unnecessary to use any electric heater. Therefore, the size and weight of the analyzer 100 can be further reduced. Furthermore, since it is possible to reduce the heating capability of the electric heater for heating the separating means, or it is unnecessary to use any electric heater, the electric power necessary to operate the analyzer 100 can be reduced.

In this embodiment, the column 8 is heated by the reforming unit 101, particularly, the combustor 5 or fuel cell 103. However, the present invention is not limited to this embodiment, and the thermal efficiency of the whole of the analyzer 100 can be optimized. For example, the heat generated during the CO reducing reaction in the CO reducer 4 can also be supplied to the column 8. For example, the analyzing unit 102 can be maintained at a constant temperature by placing the analyzing unit 102 close to the fuel cell 103 or reforming unit 101, thus increasing the measurement accuracy of the analyzing unit 102.

Note that FIG. 1 shows an example in which the reformed gas in which the CO concentration is reduced by the CO reducer 4 is supplied to the analyzing unit 102 and fuel cell 103, but the present invention is not limited to this example. For example, a hydrogen purifier 14 can be provided downstream of the CO reducer 4 in the reforming unit 101.

Figure 2:
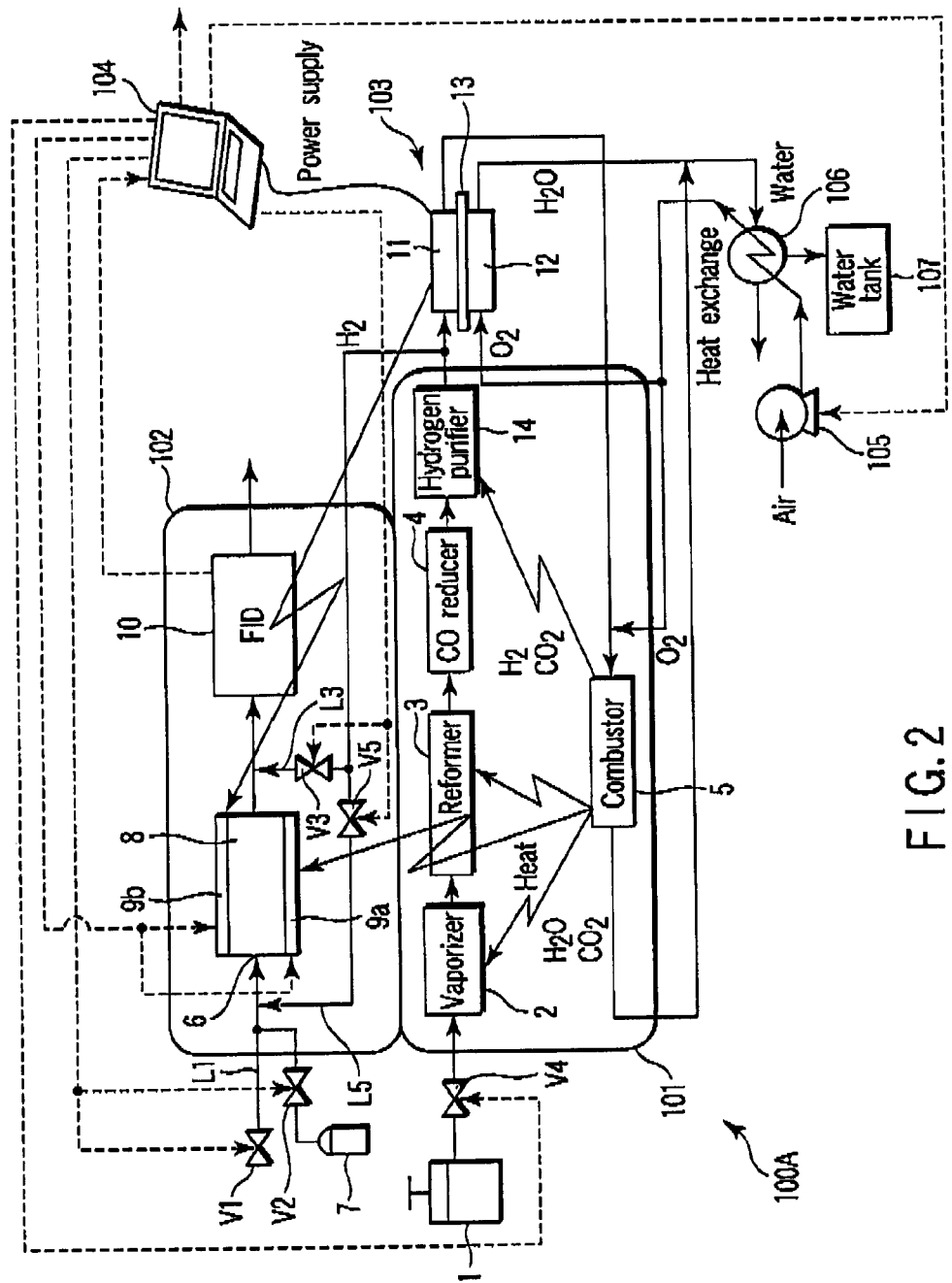
FIG. 2 is a block diagram schematically showing a modification of the analyzer according to the first embodiment of the present invention.

FIG. 2 shows an analyzer 100A as a modification additionally including the hydrogen purifier 14. If, for example, the concentration of a target gas contained in a sample gas is as low as about a few ppm, the baseline of CO contained in the reformed gas produces noise and decreases the measurement accuracy in some cases. In a case like this, the concentration of hydrogen contained in the reformed gas can be increased by further separating CO from the reformed gas by the hydrogen purifier 14. When this hydrogen-rich reformed gas is supplied to the analyzing unit 102, the measurement accuracy increases. It is also possible to keep the fuel cell 103 from decreasing its activity by CO. Note that CO separated by the hydrogen purifier 14 can be directly supplied to the combustor 5 without being supplied to the fuel electrode 11 via another line (not shown). Note that as the hydrogen purifier 14, it is possible to use a known hydrogen permeable film, e.g., a membrane of palladium, vanadium, or tantalum, or a CO sorbent. Heat can be supplied from the combustor 5 to the hydrogen purifier 14. When a palladium membrane is used as the hydrogen purifier 14, the hydrogen purifier 14 is preferably set at, e.g., about 250° C. It is possible, by heating the hydrogen purifier 14, to increase the hydrogen purification rate and further increase the hydrogen concentration of the obtained gas. A heat transfer means (not shown) can be provided between the hydrogen purifier 14 and combustor 5. Alternatively, the hydrogen purifier 14 can be stowed together with the reformer 2 and combustor 5 in a heat-insulated vessel.

Note that when a sample gas contains only one component, or when components of a sample gas are known and only changes in total amount with time are to be analyzed, the column 8 can be omitted. If the column 8 is omitted, a sample gas can be supplied directly from the supply port 6 to the FID 10.

It is also possible to supply the reformed gas to the column 8, instead of the FID 10. Alternatively, the reformed gas can be supplied to the FID 10 and column 8. As a consequence, the reformed gas can be used in a pretreatment of a sample gas as well. For example, the azo bond of azo dye and the related compounds can be cleaved and reduced to form aromatric amines by helium gas containing 5% of hydrogen, and thereby the component can be separated. Thus, the aromatic amine is produced, and it can be separated by the column 8, and analyzed by the FID 10. In this case, a switch valve V3 provided in a branch line L3 and a switch valve V5 provided in a branch line L5 can be used. The branch lines L3 and L5 are lines which branch from the reformed gas supply channel from the reforming unit 101 to the fuel cell 103. The branch line L3 joins a channel between the column 8 and FID 10. The branch line L5 joins a channel (the line L1) on the upstream side of the column 8. More specifically, to supply the reformed gas from the reforming unit 101 to the column 8, the valve V5 is opened, and the valve V3 is closed. To supply the reformed gas from the reforming unit 101 to the FID 10, the valve V3 is opened, and the valve V5 is closed. The analysis controller 104 controls these valve opening/closing operations.

Second Embodiment

Figure 3:
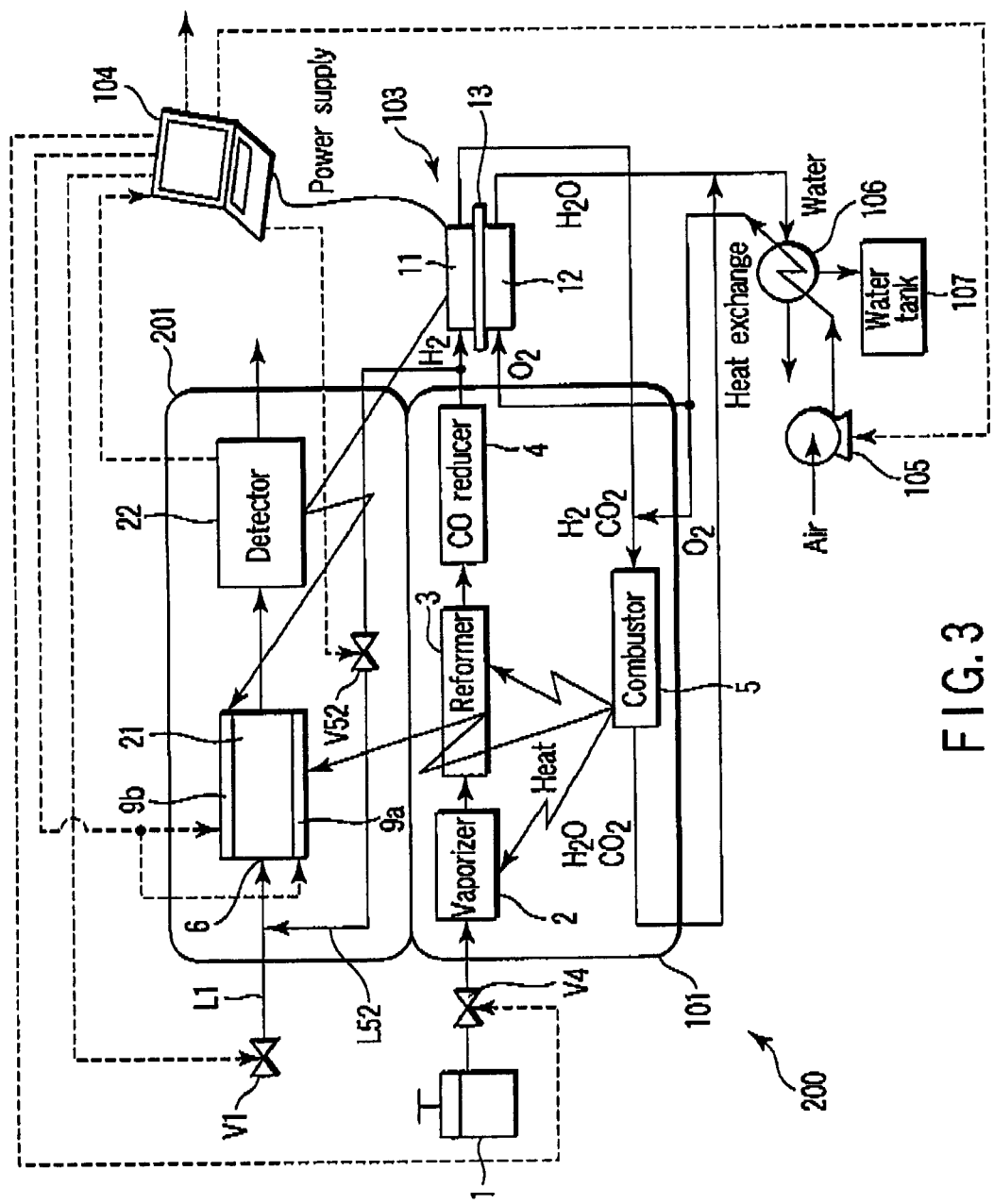
FIG. 3 is a block diagram schematically showing an analyzer according to a second embodiment of the present invention.

FIG. 3 is a block diagram schematically showing an analyzer according to a second embodiment of the present invention. Note that the same reference numerals as in the first embodiment shown in FIG. 1 denote the same parts, and an explanation thereof will be omitted.

An analyzer 200 of the second embodiment has an analyzing unit 201 which measures, for example, the atomic absorption spectrophotometric value. The analyzing unit 201 includes a reducing unit 21 and detector 22. The analyzing unit 201 identifies (qualitatively and/or quantitatively determines) components contained in a sample fluid in a liquid or gas state, together with an analysis controller 104.

For example, the detector 22 of the analyzing unit 201 detects arsenic or antimony contained in a sample fluid such as underground water.

The reducing unit 21 reduces components contained in a sample fluid by using hydrogen contained in a reformed gas supplied from a reforming unit 101. In the reducing unit 21, the reducing reaction of a sample fluid generates a hydride gas of a target component (e.g., arsenic contained in underground water) contained in a sample fluid. A bypass line L52 is provided between the reforming unit 101 and analyzing unit 201. The bypass line L52 branches from an exit-side channel of a CO reducer 4, and joins a line L1 on the upstream side of a supply port 6 of the reducing unit 21. A valve V52 is provided in the bypass line L52. When the valve V52 is opened, hydrogen gas is supplied from the CO reducer 4 to the reducing unit 21 through the bypass line L52. The analysis controller 104 controls the valve opening/closing operation.

As the detector 22, it is possible to use, e.g., a reducing vaporization atomic absorption spectroscopy photometer, or a furnace type atomic absorption spectroscopy photometer. The atomic absorption spectroscopy photometer is used to detect the absorbance by atomic absorption or spectrophotometric value of the reduced sample fluid. The atomic absorption spectroscopy photometer can detect the absorbance or spectrophotometric value of the hydride gas generated in the reducing unit 21. A detection signal obtained by the detector 22 is processed and output by the analysis controller 104.

When the analyzer 200 of the second embodiment is to be transported in order to analyze a sample fluid existing outdoors, it is unnecessary to transport hydrogen or a power supply required when a hydrogen generator electrolyzes water. This makes the analyzer 200 compact, lightweight, and easy to handle.

Note that in this embodiment, the reformed gas in which the concentration of CO is reduced by the CO reducer 4 is supplied to the analyzing unit 201 and a fuel cell 103. In this embodiment, however, a hydrogen purifier 14 can be added to the reforming unit 101 as in the first embodiment.

Also, as in the first embodiment, the reducing unit 21 can be thermally connected to the reforming unit 101 (particularly, a combustor 5) or to the fuel cell 103 by using a heat conducting member 9a or 9b. The reducing reaction in the reducing unit 21 can be accelerated by controlling the temperature of the reducing unit 21 by using heat which is conducted through the heat conducting member 9a or 9b. In addition, the heat of the combustor 5 or fuel cell 103 can be conducted to the detector 22 via a heat transfer means (not shown). This makes it possible to reduce the temperature change in the detector 22, and thereby increase the detection accuracy. As described above, the analyzer of this embodiment is also suited to maintaining the measurement systems 21 and 22 at a constant temperature, and this increases the thermal efficiency.

Third Embodiment

Figure 4:
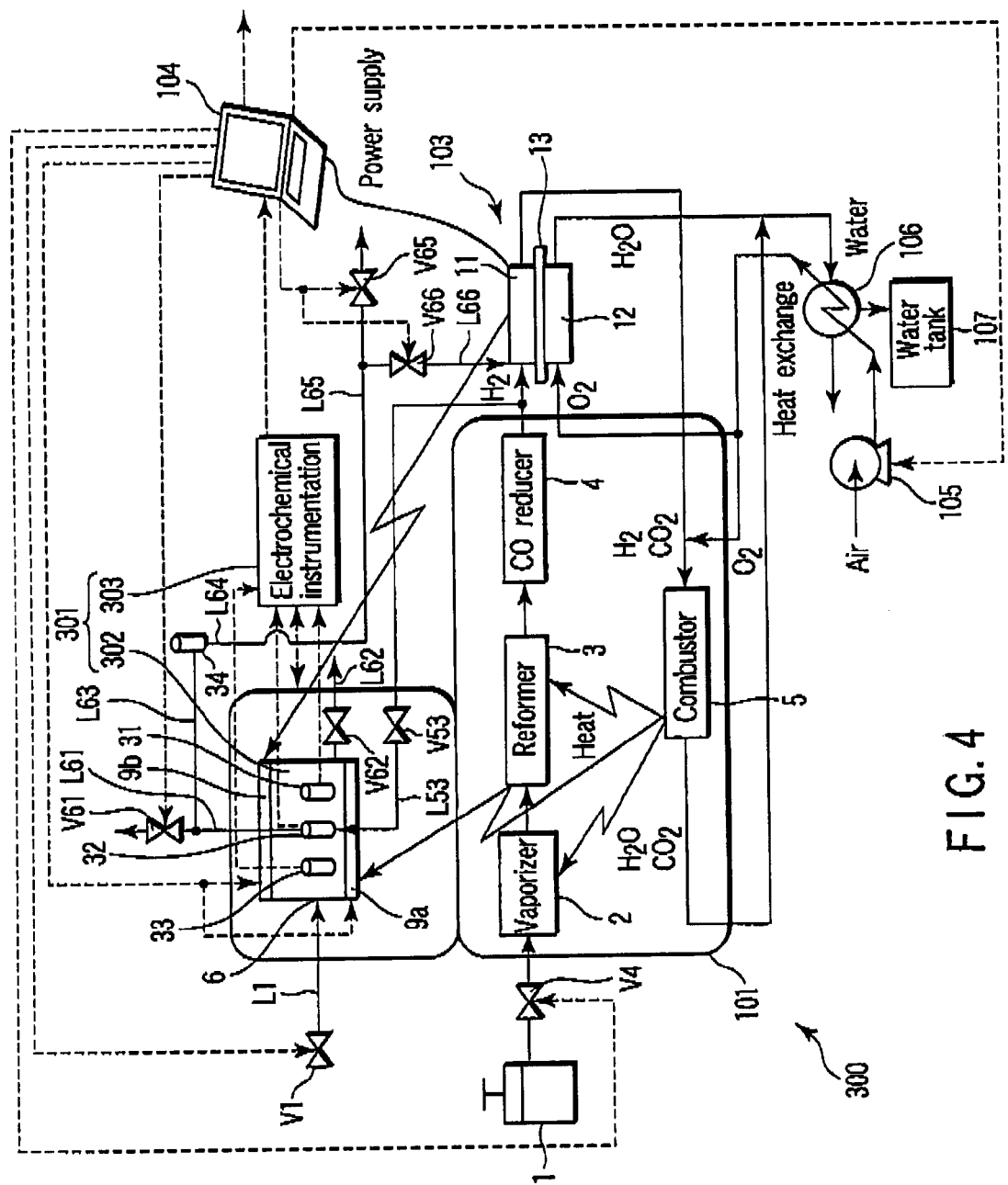
FIG. 4 is a block diagram schematically showing an analyzer according to a third embodiment of the present invention.

FIG. 4 is a block diagram schematically showing an analyzer according to a third embodiment of the present invention. Note that the same reference numerals as in the above embodiments denote the same parts, and an explanation thereof will be omitted.

An analyzer 300 of the third embodiment has an analyzing unit 301 which performs electrochemical measurements. The analyzing unit 301 includes an electrochemical cell 302 and electrochemical instrumentation 303. The electrochemical cell 302 includes a working electrode (WE) 31, reference electrode (RE) 32, and counter electrode (CE) 33. The working electrode (WE) 31, reference electrode (RE) 32, and counter electrode (CE) 33 are dipped in a sample liquid. The electrochemical instrumentation 303 transmits and receives signals with the working electrode (WE) 31, reference electrode (RE) 32, and counter electrode (CE) 33 of the electrochemical cell 302. The analyzing unit 301 also has a potentiostat (PS) (not shown) or a galvanostat (GS) (not shown). The potentiostat (PS) controls the electric potential of the working electrode 31 with respect to the reference electrode 32 at a preset potential. The galvanostat (GS) controls an electric current flowing between the working electrode 31 and counter electrode 33 at a preset current value. In addition, the analyzing unit 301 has, if necessary, a function generator (not shown) which temporally controls these electric potential and electric current. The analyzing unit 301 identifies (qualitatively and/or quantitatively determines) components contained in a sample fluid in a liquid state, together with an analysis controller 104. Note that a sample fluid supplied to the analyzing unit 301 can be either a continuous flow system or intermittent batch system.

The reference electrode 32 contains, e.g., a platinum black electrode obtained by plating a platinum electrode with platinum, and a Luggin probe which reduces the influence of iR drop. The reference electrode 32 is connected to the exit of a reforming unit 101 by a bypass line L53. A valve V53 is provided in the line L53. Hydrogen gas in a reformed gas generated in the reforming unit 101 is supplied to the reference electrode 32 through the line L53 by opening the valve V53, and bubbled to the platinum black electrode in the reference electrode 32. This makes it possible to set the electric potential of the platinum black electrode at the hydrogen potential. A sample solution (a sample liquid) is used as an electrolyte contained in the reference electrode 32. The reference electrode 32 functions as a reversible hydrogen electrode (RHE). This reversible hydrogen electrode is preferable because it is unnecessary to take account of the liquid junction potential and the like.

The electrochemical instrumentation 303 is connected to the working electrode (WE) 31, reference electrode (RE) 32, counter electrode (CE) 33, and analysis controller 104. The electrochemical instrumentation 303 applies a predetermined electric potential based on the reference electrode 32 to the working electrode 31. The electrochemical instrumentation 303 detects changes in electric current between the working electrode 31 and counter electrode 33. On the basis of this detection signal, the analysis controller 104 provides data capable of specifying the composition of a sample fluid or the concentration of an analytic component. The electrochemical instrumentation 303 also performs control necessary to operate the electrochemical cell 302, e.g., controls the permutating samples, controls the system temperatures, and transmits and receives data with the electrochemical cell 302. Although chronoamperometry is explained in this embodiment, chronopotentiometry can also be performed. Specifically, the system temperatures are, e.g., temperatures of liquid contained in the electrochemical cell 302 or normal hydrogen electrode cell 304 explained below.

A sample fluid having undergone the electrochemical measurement is exhausted outside the electrochemical cell 302 through a line L62 by opening a valve V62. On the other hand, hydrogen gas used in the measurement can be exhausted outside the electrochemical cell 302, or returned to a fuel cell 103 and reused. The flow of the hydrogen gas used in the measurement will be explained below.

A valve V61 is provided in a line L61 which is connected to the reference electrode (RE) 32, and extends outside the electrochemical cell 302. By opening the valve V61, the hydrogen gas can be exhausted outside the electrochemical cell 302. The line L61 branches into branch line L63, and a trap 34 is provided in this branch line L63. The trap 34 removes mist and contaminants contained in the hydrogen gas used in the measurement. An exit-side line L64 of the trap 34 branches into two lines, and each branch line communicates with the outside of the analyzer 300 and the fuel cell 103. A valve V65 is provided in a branch line L65 which communicates with the outside of the analyzer 300. Also, a valve V66 is provided in a branch line L66 which communicates with the fuel cell 103. The hydrogen gas used in the measurement can be supplied to the trap 34 by closing the valve V61. For example, if the contamination concentration in the hydrogen gas used in the measurement is excessively high, the hydrogen gas from which the contaminants is removed by the trap 34 can be exhausted outside the analyzer 300 by opening the valve V65 and closing the valves V66. Likewise, the hydrogen gas can be supplied to the fuel cell 103 by opening the valve V66 and closing the valves V65. Whether to exhaust the hydrogen gas or supply the hydrogen gas to the fuel cell 103 can be determined on the basis of, e.g., the hydrogen concentration and contamination concentration in the hydrogen gas. This determination and the valve control can be performed by the analysis controller 104.

Note that in this embodiment, the most basic arrangement of the three-electrode cell type, current-potential curve (polarization curve) measurement is explained as the electrochemical cell 302. When the analyzer according to the embodiment of the present invention is used, it is possible to perform measurements by, e.g., anodic stripping voltammetry (AVS) and adorptive cathodic stripping voltammetry (ACSV), in addition to general cyclic voltammetry.

The embodiment, however, is not limited to the above measurements. For example, AC impedance measurement can be performed by connecting an impedance analyzer (a frequency response analyzer [FRA]) to the above embodiment.

When the analyzer 300 of the third embodiment is to be transported in order to analyze a sample fluid existing outdoors, it is unnecessary to transport hydrogen or a power supply required when a hydrogen generator electrolyzes water. This makes the analyzer 300 compact, lightweight, and easy to handle.

Note that in FIG. 4, the reformed gas in which the concentration of CO is reduced by the CO reducer 4 is supplied to the analyzing unit 301 and fuel cell 103. In this embodiment, however, a hydrogen purifier 14 can be provided as in the first embodiment.

Also, as in the first embodiment, the electrochemical cell 302 can be connected to the reforming unit 101 (particularly, a combustor 5) or to the fuel cell 103 by using a heat conducting member 9a or 9b. By controlling the temperature of the electrochemical cell 302 by using heat which is conducted through the heat conducting member 9a or 9b, it is possible to maintain a sample fluid at a constant temperature, and increase the measurement accuracy of the electrochemical cell 302. As described above, the analyzer of this embodiment is also suited to maintaining the electrochemical cell 302 at a constant temperature, and this increases the thermal efficiency.

Figure 5:
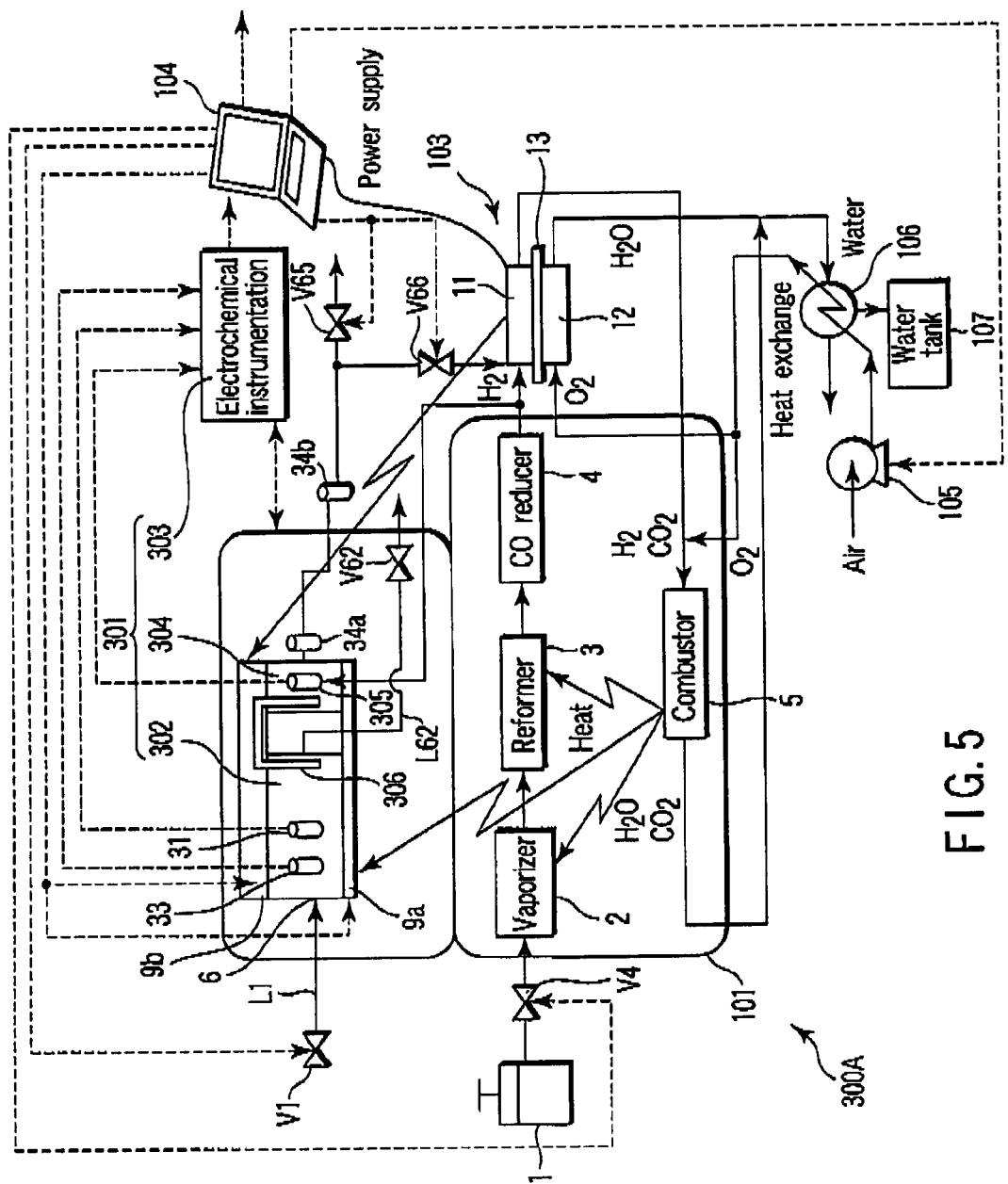
FIG. 5 is a block diagram schematically showing a modification of the analyzer according to the third embodiment of the present invention.

In addition, a normal hydrogen electrode cell 304 can be connected to the electrochemical cell 302 via salt bridge 306. The normal hydrogen electrode (NHE) cell 304 includes normal hydrogen electrode (NHE) 305. Thus, the normal hydrogen electrode (NHE) 305 is indirectly connected to the sample liquid electrically, instead of a reference electrode. FIG. 5 shows an analyzer 300A as a modification including a normal hydrogen electrode (NHE) cell 304. The reformed gas is supplied to the NHE 305 of the NHE cell 304. Hydrogen gas used in the NHE cell 304 is exhausted from the analyzer 300A or supplied to the fuel cell 103, after passed through traps 34a and 34b. Although this modification uses the two traps 34a and 34b, the number of traps can also be one or two or more. In the analyzer 300A using the normal hydrogen electrode (NHE) cell 304, particularly the gas composition returned to the fuel cell 103 becomes constant and stable. This is so because the NHE 305 can be placed separately from the electrochemical cell 302 to which a sample fluid is supplied. Therefore, this analyzer is a more favorable analytical system from the viewpoint of the reuse of hydrogen gas.

Note that a single heat conducting member 9a or 9b is preferably provided in the electrochemical cell 302 and NHE cell 304. This makes it possible to reduce the temperature difference between the electrochemical cell 302 including working electrode (WE) 31 and counter electrode (CE) 33, and NHE cell 304 including normal hydrogen electrode (NHE) 305, and increase the measurement accuracy. As described above, the analyzer of this embodiment is also suited to maintaining the measurement systems 302 and 304 at a constant temperature, and this increases the thermal efficiency. In this embodiment, the hydrogen purifier 14 can be arranged as in the first embodiment. In this case, the reformed gas in which CO concentration is reduced is supplied to the reference electrode 32 or normal hydrogen electrode 305, thereby further improving the measurement accuracy.

Fourth Embodiment

FIG. 6 is a block diagram schematically showing an analyzer according to a fourth embodiment of the present invention. Note that the same reference numerals as in the above embodiments denote the same parts, and an explanation thereof will be omitted.

An analyzer 400 of the fourth embodiment has an analyzing unit 401 which separates and analyzes a sample fluid (mixture) by using chromatography. The analyzing unit 401 includes a separator 42 and detector 43. In addition, a pressurizing means 41 connected to a fuel tank 1 is provided in a line L1 on the upstream side of the analyzing unit 401. The pressurizing means 41 applies a pressure to a sample fluid in a liquid state which flows through the line L1. The pressurized sample fluid is supplied to the separator 42 having a separating means through a supply port 6.

The fuel tank 1 stores fuel. The fuel tank 1 also stores a pressurizing agent for obtaining a pressure for supplying the fuel to a reforming unit 101. Methanol, naphtha, or the like as the fuel is in a liquid state in the operation environment of the analyzer 400. The liquid fuel is supplied to the reforming unit 101 by using the pressure obtained by the pressurizing agent. Note that if the fuel contains a gaseous compound, such as dimethylether, in the operation environment of the analyzer 400, this dimethylether or the like can be used as the pressurizing agent to supply the fuel. When dimethylether is used as the pressurizing agent, the pressurizing agent can be supplied as a part of the fuel to the reforming unit 101. That is, dimethylether functions not only as the pressurizing agent but also as a part of the fuel.

The pressurizing means 41 applies a pressure to a sample fluid which flows through the line L1, by using the pressure of the pressurizing agent stored in the fuel tank 1. To supply a sample fluid in a liquid state to the separator 42 and separate the sample fluid, it is necessary to apply a pressure higher than that of the analyzer 100 described in the first embodiment. When the operation environment of the analyzer 400 is at room temperature and an atmospheric pressure, a pressure of about 6 kgf/cm$^2$ can be generated by storing, e.g., dimethylether in a liquid state in the fuel tank 1. The pressurizing means 41 uses this pressure to supply a sample fluid to the separator 42 and separate the sample fluid. That is, dimethylether functions not only as a pressurizing agent for supplying the fuel to the reforming unit 101, but also as a pressurizing agent for supplying a sample fluid into the separator 42.

The fuel supplied from the fuel tank 1 is once stored in the pressurizing means 41. In this state, the pressurizing means 41 generates a sufficient pressure. After that, the fuel is supplied from the pressurizing means 41 to the reforming unit 101. The whole or a part of the fuel remaining in the pressurizing means 41 can be supplied to the reforming unit 101. A part of the fuel to be supplied to the reforming unit 101 may also be returned to the pressurizing means 41. A valve V10 is provided in a line L10 which communicates with the pressurizing means 41 and reforming unit 101. A branch line L11 branches from the line L10. The branch line L11 joins the line L1 on the upstream side of the pressurizing means 41. A valve V11 is provided in the branch line L11. The flow rate of the fuel supplied to the reforming unit 101 and the flow rate of the fuel returned to the pressurizing means 41 can be controlled by controlling the valves V10 and V11 by an analysis controller 104.

The separator 42 separates components contained in a sample fluid under predetermined separation conditions. The separator 42 includes a column for use in, e.g., high performance liquid chromatography (HPLC) which utilizes a pressure, or ion chromatography (IC) which utilizes electrochemical characteristics.

When high-performance liquid chromatography (HPLC) or ion chromatography (IC) is used, an appropriate separation mode is in many cases selected in accordance with a type of sample fluid. In the case of an ion exchange separation mode, an ion exchange resin packed column which is packed with ion exchange resins is selected as the column. A target ionic component contained in a sample fluid can be separated by the difference in the selectivity coefficients of the packed ion exchange resins.

The separation mode in the present invention is, of course, not limited to the ion exchange separation mode. For example, it is also possible to apply a reversed phase mode, normal phase mode, ligand exchange mode, ion exclusion mode, GPC mode, GFC mode, multi mode, affinity mode, or optical resolution mode, in accordance with a sample fluid.

The detector 43 selectively detects the component in the sample fluid separated by the separator 42. The detector 43 outputs a signal indicating, e.g., the electric conductivity of the detected component in the sample fluid to the analysis controller 104. On the basis of the analytical result, the analysis controller 104 can identify (qualitatively and/or quantitatively determine) the analytical component. For example, an electric conductivity detector outputting a signal representing electric conductivity, or a detector using a spectroscopic means, can be used as the detector 43. The spectroscopic means is, e.g., an Absorption Spectrophotometer.

When the analyzer 400 of the fourth embodiment is to be transported in order to analyze a sample fluid existing outdoors, it is unnecessary to transport a power supply required when the analysis controller 104 processes an output signal from the detector 43. In addition, dimethyl-ether usable as a part of the fuel can also be used as a pressurizing agent which generates a pressure for supplying the fuel to the reforming unit 101, and supplying a sample fluid to the separator 42. This makes the analyzer 400 compact, lightweight, and easy to handle.

Note that in this embodiment, a reformed gas in which the CO concentration is reduced by a CO reducer 4 is supplied to a fuel cell 103. In this embodiment, however, a hydrogen purifier 14 can be added to the reforming unit 101 as in the first embodiment.

Also, as in the first embodiment, the separator 42 can be connected to the reforming unit 101 (particularly, a combustor 5) or to the fuel cell 103 by using a heat conducting members 9a or 9b. The separator 42 can be heated to a temperature suited to component separation by using heat which is conducted through the heat conducting member 9a or 9b. Also, the heat of the combustor 5 or fuel cell 103 can be conducted to the detector 43 via a heat transfer means (not shown). This makes it possible to reduce the temperature change of the detector 43, and further increase the detection accuracy. As described above, the analyzer of this embodiment is also suited to maintaining the measurement systems 42 and 43 at a constant temperature, and this increases the thermal efficiency.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An analyzer comprising:
   a reforming unit which reforms a fuel containing an organic compound, which contains carbon and hydrogen, into a reformed gas containing hydrogen;
   a flame ionization detector which is connected to the reforming unit, detects an ion generated by combining and combusting the reformed gas supplied from the reforming unit and a sample gas, or ionizing the sample gas by combining and reacting with the reformed gas supplied from the reforming unit, and outputs an output signal representing the ionic amount; and
   an analysis controller which analyzes the output signal from the flame ionization detector, and provides data configured to identify a component contained in the sample gas.

2. An analyzer according to claim 1, wherein the analysis controller controls an amount of at least one of the sample gas, the reformed gas, or the sample gas and the reformed gas, to be supplied to the flame ionization detector.

3. An analyzer according to claim 1, further comprising separating means for separating a component contained in the sample gas before the sample gas is supplied to the flame ionization detector.

4. An analyzer according to claim 1, further comprising a gas chromatography column which separates a component contained in the sample gas before the sample gas is supplied to the flame ionization detector.

5. An analyzer according to claim 1, further comprising:
   a fuel cell which is connected to the reforming unit, and generates power by using the reformed gas supplied from the reforming unit and oxygen; and
   a combustor which is connected to the fuel cell, and accelerates a combustion reaction of the reformed gas exhausted from the fuel cell.

6. An analyzer according to claim 1, further comprising:
   a fuel cell which is connected to the reforming unit, and generates power by using the reformed gas supplied from the reforming unit and oxygen;
   a CO reducer which reduces CO of the reformed gas before the sample gas is supplied to the fuel cell;
   separating means for separating a component contained in the sample gas before the sample gas is supplied to the flame ionization detector;
   a combustor which is connected to the fuel cell, and accelerates a combustion reaction of the reformed gas exhausted from the fuel cell; and
   heat transfer means for transferring, to the separating means, at least one of heat generated by the combustion reaction in the combustor, heat generated by the CO reducing reaction in the CO reducer, and heat generated by the power generation in the fuel cell.

7. An analyzer according to claim 1, further comprising:
   a fuel cell which is connected to the reforming unit, and generates power by using the reformed gas supplied from the reforming unit and oxygen;
   separating means for separating a component contained in the sample gas before the sample gas is supplied to the flame ionization detector;
   a combustor which is connected to the fuel cell, and accelerates a combustion reaction of the reformed gas exhausted from the fuel cell;
   a first heat conducting member which conducts, to the separating means, at least a part of heat generated by the combustion reaction in the combustor; and
   a second heat conducting member which conducts, to the separating means, at least a part of heat generated by the power generation in the fuel cell, and
   in which the analysis controller selects one of heat conduction by the first heat conducting member and heat conduction by the second heat conducting member in accordance with the component contained in the sample gas.

8. An analyzer according to claim 1, further comprising a hydrogen purifier which increases a hydrogen concentration in the reformed gas before being supplied to the flame ionization detector.

* * * * *